United States Patent [19]
Bohen et al.

[11] 4,115,352
[45] Sep. 19, 1978

[54] HEAT STABILIZER COMPOSITION FOR HALOGENATED RESINS

[75] Inventors: Joseph Michael Bohen, King of Prussia; Sameeh Said Toukan, Phoenixville, both of Pa.

[73] Assignee: Pennwalt Corporation, Philadelphia, Pa.

[21] Appl. No.: 799,862

[22] Filed: May 23, 1977

[51] Int. Cl.$^2$ ............... C08K 5/59; C08K 5/58; C08K 5/36
[52] U.S. Cl. ............... 260/45.75 B; 252/406; 260/45.7 R; 260/45.7 S; 260/45.85 H; 260/45.85 S; 260/45.75 S; 260/23 XA
[58] Field of Search ............... 252/406; 260/45.7 S, 260/45.85 S, 45.85 H, 45.75 S, 45.75 B, 45.7 R, 23 XA

[56] References Cited

U.S. PATENT DOCUMENTS

| | | | |
|---|---|---|---|
| 2,050,843 | 8/1936 | Jacobsohn | 260/45.7 S |
| 2,723,965 | 11/1955 | Leistner et al. | 260/45.7 R |
| 3,147,232 | 9/1964 | Norman et al. | 260/23 XA |
| 3,297,629 | 1/1967 | Kauder | 260/45.7 S |
| 3,398,114 | 8/1968 | Pollock | 260/45.7 S |
| 3,764,571 | 10/1973 | Jennings et al. | 260/23 XA |
| 3,787,357 | 1/1974 | Brecker | 260/45.7 S |
| 3,803,083 | 4/1974 | Brecker | 260/23 XA |
| 3,887,508 | 6/1975 | Dieckmann | 260/45.75 B |
| 3,928,285 | 12/1975 | Gough et al. | 260/45.7 S |

*Primary Examiner*—V. P. Hoke

[57] ABSTRACT

Mixtures of alkali and alkaline earth metal salts of mercaptans or mercapto acids with specified sulfur containing organotin or antimony compounds are disclosed herein as heat stabilizers for halogenated resins.

18 Claims, No Drawings

HEAT STABILIZER COMPOSITION FOR HALOGENATED RESINS

THE INVENTION

The use of sulfur-containing organotin compounds as heat stabilizers for halogenated resins is well known. Although the organotin compounds are the most effective stabilizers, they unfortunately have the disadvantage of being the most expensive. It would be of significance, therefore, to provide materials that can extend the performance of these stabilizers.

It has now been discovered that certain alkali and alkaline earth metal salts of mercapians or mercapio acids unexpectedly improve the performance of sulfur-containing organotin and sulfur-containing antimony compounds in the heat stabilization of halogenated resins. The combination provides a stabilizer system which permits more efficient use of the organotin or antimony compound, thus offering resin formulators excellent stabilization at a substantially reduced cost. The salts are particularly valuable in three-component systems (salt, sulfur - containing organotin or antimony stabilizer, and an overbased organic complex of an alkali or alkaline earth metal base) because still greater reductions in cost are possible.

Accordingly, this invention is a composition comprising a mixture of (a) an alkali or alkaline earth metal salt of a mercaptan or mercapto acid and (b) a sulfur-containing organotin compound having a $$-\overset{|}{\underset{|}{C}}-Sn-S$$

group or a sulfur-containing antimony compound having a Sb — S group, said mixture having a weight ratio of (a) to (b) ranging between about 0.05:1 and about 3:1. Additionally, the composition may also contain an over-based organic complex of an alkali or alkaline earth metal carbonate in an amount sufficient to provide additional heat stability to a halogenated resin to which said composition may be added.

Alkali and alkaline earth metal salts of mercaptans and mercapto acids which are operable in this invention are described by the formulas:

$$M(SR)_n \quad MSR^1\overset{Y}{\underset{\|}{C}}XM \quad M^1\overset{S}{\underset{X}{\diagup\diagdown}}\overset{R^1}{\underset{C=Y}{|}}$$

$$\text{I} \quad\quad \text{II} \quad\quad \text{III}$$

wherein: M is a Group IA metal (an alkali metal, in which case $n=1$) or a group IIA metal (an alkaline earth metal, in which case $n=2$) ; $M^1$ is a group IIA metal. R is a hyrocarbon radical (e.g., alkyl, cycloalkyl, aryl, or mixed alkyl-aryl) having 1-22 carbon atoms, optionally substituted by halogen, —XH, —$XR^2$, $$-X-\overset{Y}{\underset{\|}{C}}R^2, \text{ or } -\overset{Y}{\underset{\|}{C}}XR^2$$

where $R^2$ is a 1-20 carbon atom alkyl, alkenyl, cycloalkyl, aryl, or mixed alkyl-aryl group ; X and Y are independently selected from O and S; and $R^1$ is a hydrocarbon linking group having 1-6 carbon atoms (which may be part of an attached cyclic structure) and is optionally substituted with halogen, —XH, —$XR^2$, $$-X-\overset{Y}{\underset{\|}{C}}R^2, \text{ or } -\overset{Y}{\underset{\|}{C}}XR^2$$

where $R^2$ is as described above.

In the preparation of compounds of structure III, there might be formed "polymeric" linear salts of the same empirical formula, and these mixtures are operable and included in this invention.

Compositions containing more than one metal, and compositions having mixed R, $R^1$ and $R^2$ groups, are also operable and part of this invention.

Examples of these alkali and alkaline earth metal salts of mercaptans and mercapto acids are:

$NaSCH_3$ $NaSC_4H_9$ $NaSC_{12}H_{25}$ $NaS\text{—}\langle\bigcirc\rangle$ $KSC_2H_5$ $KS\text{—}\langle S\rangle$ $KSCH_2\text{—}\langle\bigcirc\rangle$ $KSC_8H_{17}$ $NaSC_2H_4SH$ $Ba(S\text{—}\langle S\rangle)_2$ $Ba(SCH_2\text{—}\langle\bigcirc\rangle)_2$ $Ba(SC_{12}H_{25})_2$ $Ba(SC_8H_{17})_2$ $Ba(SC_{20}H_{41})_2$ $Ba(SC_8H_{17})_{1.0}(SC_{12}H_{25})_{1.0}$ $Ba[S\text{—}\langle\bigcirc\rangle\langle\bigcirc\rangle]_2$ $Mg(SC_{12}H_{25})_2$ $Ba(SC_2H_4S_2CC_{17}H_{35})_2$ -continued

| | |
|---|---|
| Ba(SC$_2$H$_4$SCH$_3$)$_2$ | Ca[SC$_2$H$_4$SC(O)C$_{17}$H$_{33}$]$_2$ |
| Mg(SC$_2$H$_4$SC$_8$H$_{17}$)$_2$ | Ba(SC$_4$H$_8$S$_2$C—⟨O⟩)$_2$ |
| | Ba[SC$_2$H$_4$OC(S)C$_4$H$_9$]$_2$ |
| K(SCH$_3$)$_{0.5}$(SC$_6$H$_{13}$)0.5 | Mg(SCH$_2$CHC$_4$H$_9$)$_2$<br>               \|<br>               C$_2$H$_5$ |
| Ca(SCH$_3$)$_2$ | |
| | Mg(S—⟨O⟩)$_2$ |
| Ca(SCH$_2$—⟨O⟩)$_2$ | Mg(S—⟨O⟩—CH$_3$)$_2$ |
| Ca(SC$_{12}$H$_{25}$)$_2$ | NaSCHCO$_2$C$_4$H$_9$<br>       \|<br>       CH$_2$CO$_2$C$_4$H$_9$ |
| Ca(SC$_{10}$H$_{21}$)$_2$ | NaSCHCO$_2$C$_3$H$_7$<br>       \|<br>       CO$_2$C$_3$H$_7$ |
| | KSCH$_2$CO$_2$C$_8$H$_{17}$ |
| Ca(SC$_{12}$H$_{25}$)$_{1.0}$(S—⟨O⟩)$_{1.0}$ | |
| Sr(SC$_{12}$H$_{25}$)$_2$ | KSCH$_2$CH$_2$CO$_2$C$_2$H$_5$ |
| Sr(S—⟨O⟩)$_2$ | KSCHCO$_2$C$_4$H$_9$<br>   \|<br>   CH$_2$CO$_2$C$_4$H$_9$ |
| Sr(SC$_8$H$_{17}$)$_2$ | Ca(SCH$_2$CO$_2$C$_{10}$H$_{21}$)$_2$ |
| NaSC$_3$H$_6$OH | Ca(SCH$_2$CH$_2$CO$_2$C$_8$H$_{17}$)$_2$ |
| Ba(SC$_{10}$H$_{20}$OH)$_2$ | Ca(SCH$_2$CH$_2$CO$_2$C$_8$H$_{17}$)$_{1.0}$(SCH$_2$CO$_2$C$_8$H$_{17}$)$_{1.0}$ |
| KSC$_2$H$_4$OH | Ca(SCHCO$_2$C$_2$H$_5$)$_2$<br>   \|<br>   CH$_2$CO$_2$C$_2$H$_5$ |
| Ca(SCH$_2$CHCH$_2$)$_2$<br>       \|  \|<br>      OH OH | Ba(SCH$_2$CO$_2$C$_8$H$_{17}$)$_2$ |
| NaSC$_2$H$_4$O$_2$C—⟨O⟩ | Ba(SCH$_2$CH$_2$CO$_2$C$_8$H$_{17}$)$_2$ |
| NaSC$_2$H$_4$O$_2$CC$_{17}$H$_{35}$ | Ba(SCH$_2$CH$_2$CO$_2$C$_{10}$H$_{21}$)$_{1.0}$(SCH$_2$CO$_2$C$_{10}$H$_{21}$)$_{1.0}$ |
| NaSC$_2$H$_4$O$_2$CC$_{17}$H$_{33}$<br>Ba(SC$_2$H$_4$O$_2$CC$_{17}$H$_{33}$)$_2$ | Ba(SCH$_2$CH$_2$CO$_2$C$_8$H$_{17}$)$_{0.5}$(SCH$_2$CO$_2$C$_8$H$_{17}$)$_{1.5}$ |
| Ba(SC$_2$H$_4$O$_2$CC$_{17}$H$_{35}$)$_2$ | |
| Ba(SC$_3$H$_6$O$_2$C—⟨S⟩)$_2$ | Ba(SCHCO$_2$C$_4$H$_9$)$_2$<br>   \|<br>   CH$_2$CO$_2$C$_4$H$_9$ |
| Ca(SC$_2$H$_4$O$_2$CC$_{17}$H$_{33}$)$_2$ | |
| Ca(SC$_2$H$_4$O$_2$CC$_{17}$H$_{35}$)$_2$ | Mg(SCH$_2$CO$_2$C$_{20}$H$_{41}$)$_2$ |
| Ca(SC$_3$H$_6$O$_2$CC$_{17}$H$_{29}$)$_2$ | Mg(SCH$_2$CH$_2$CO$_2$C$_8$H$_{17}$)$_2$ |
| Ca(SCH$_2$CHCH$_2$O$_2$CCH$_3$)$_2$<br>        \|<br>       O$_2$CCH$_3$ | Sr(SCH$_2$CO$_2$C$_{12}$H$_{25}$)$_2$ |
| Ba(SC$_2$H$_4$OC$_2$H$_5$)$_2$ | Sr(SCH$_2$CH$_2$CO$_2$C$_3$H$_7$)$_2$ |
| Ca(SC$_3$H$_6$OC$_2$H$_5$)$_2$ | Ba⟨S—CH$_2$ \| O—C=O⟩ |
| NaSCH$_2$CO$_2$C$_8$H$_{17}$ | Ba⟨S—CH$_2$ \ CH$_2$ / O—C=O⟩ |

-continued

NaSCH₂CH₂CO₂C₁₂H₂₅

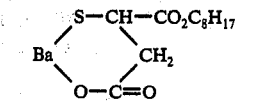

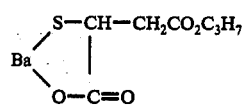

Na(SCH₂CH₂CO₂C₈H₁₇)₀.₅(SCH₂CO₂C₈H₁₇)₀.₅

NaSCH₂CO₂Na

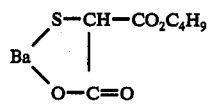

NaSCH₂CH₂CO₂Na

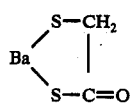

NaSCHCH₂CO₂Na
  |
CO₂C₂H₅

KsCH₂CO₂K

KSCH₂CH₂CO₂K

KSCHCO₂K
  |
CO₂C₄H₉

KSCH₂C(=O)—SK

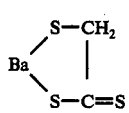

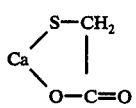

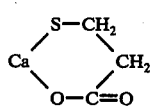

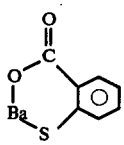

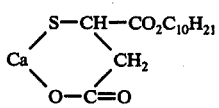

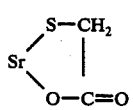

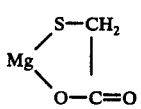

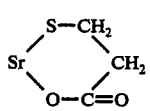

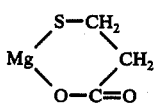

Particularly preferred compounds are:

| | |
|---|---|
| NaSCH₂CO₂C₈H₁₇ | Ca(SCH₂CO₂C₈H₁₇)₂ |
| NaSCH₂CH₂CO₂C₈H₁₇ | Ca(SCH₂CH₂CO₂C₈H₁₇)₂ |
| NaSC₁₂H₂₅ | Ca(SC₂H₄O₂CC₁₇H₃₅)₂ |
| NaSCH₂CO₂Na | Ca(SC₂H₄O₂CC₁₇H₃₃)₂ |
| NaSCH₂CH₂CO₂Na | Ca(SC₁₂H₂₅)₂ |

-continued

NaSCHCO₂C₄H₉
  |
CH₂CO₂C₄H₉

Ba(SC₁₂H₂₅)₂

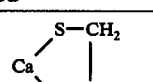

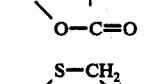

-continued

| | |
|---|---|
| Ba(SCH$_2$CO$_2$C$_8$H$_{17}$)$_2$ | Ca(SCHCO$_2$C$_4$H$_9$)$_2$<br>    |<br>   CH$_2$CO$_2$C$_4$H$_9$ |
| Ba(SCH$_2$CH$_2$CO$_2$C$_8$H$_{17}$)$_2$ | Ba(SC$_2$H$_4$O$_2$CC$_{17}$H$_{33}$)$_2$ |
| Ba(SC$_2$H$_4$O$_2$CC$_{17}$H$_{35}$)$_2$ | |
| Ba⟨S—CH$_2$ / O—C=O⟩ | Ba⟨S—CH$_2$ / CH$_2$ / O—C=O⟩ |
| Ba(SCHCO$_2$C$_4$H$_9$)$_2$<br>   |<br>  CH$_2$CO$_2$C$_4$H$_9$ | |

Especially preferred because of their superior performance are the barium and calcium salts

| | |
|---|---|
| Ba(SCH$_2$CO$_2$C$_8$H$_{17}$)$_2$ | Ba(SCH$_2$CH$_2$CO$_2$C$_8$H$_{17}$)$_2$ |
| Ba(SC$_2$H$_4$O$_2$CC$_{17}$H$_{35}$)$_2$ | Ba(SC$_2$H$_4$O$_2$CC$_{17}$H$_{33}$)$_2$ |
| Ca(SCH$_2$CO$_2$C$_8$H$_{17}$)$_2$ | Ca(SCH$_2$CH$_2$CO$_2$C$_8$H$_{17}$)$_2$ |
| Ca(SC$_2$H$_4$O$_2$CC$_{17}$H$_{35}$)$_2$ | Ca(SC$_2$H$_4$O$_2$CC$_{17}$H$_{33}$)$_2$ |

The synergistic compounds of this invention can be conveniently prepared by the reaction of selected mercaptans or mercapto acids with a basic salt of the selected alkali or alkaline earth metal (oxide, hydroxide, or alkoxide) in an appropriate solvent.

The sulfur-containing organotin compounds which are of use in this invention are generally characterized as having a sulfur-containing radical or atom attached to the tin through the sulfur atom and a hydrocarbon or substituted hydrocarbon group directly attached to the tin through a carbon atom, i.e., compounds containing the $$-\underset{|}{\overset{|}{C}}-Sn-S$$

group. The tin bonds are usually derived from polyvalent tin by having at least one valence for bonding to the sulfur atom while the remaining valence or valences are for bonding with the hydrocarbon radical. Tin usually exists as a bi- or tetraatom, but coordination complexes of tin are known where the tin behaves in even higher valence state and therefore, the valence state of tin can vary in the organotin compounds which can be used in this invention.

Generally however, most organotins suitable for use in this invention are derived from tetravalent tin. The types of organotin compounds contemplated, are those reviewed in U.S. Pat. No. 3,764,571, column 3, line 1 to column 5 line 55; U.S. Pat. No. 2,641,588, column 1, lines 32-53 to column. 2, lines 13-46; U.S. Pat. No. 2,641,596 column 1, lines 10-44; U.S. Pat. No. 2,726,254, column 1, line 63 to column 2, line 19; U.S. Pat. No. 2,789,963, column 2, lines 35-60; U.S. Pat. No. 2,914,506, column 1, line 59 to column 4, line 8; U.S. Pat. No. 2,870,119, column 1, lines 27-53 and U.S. Pat. No. 3,126,400 column 1, lines 21-61. Other patents exemplifying organotin sulfur-containing compounds include U.S. Pat. Nos. 3,069,447; 3,478,071; 2,998,441; 2,809,956; 3,293,273; 3,396,185; 3,485,794; 2,830,067; and 2,855,417.

Other organotin sulfur-containing compounds which are within the scope of this invention are characterized by the following Formula IV.

$$(R^3SnS_{1.5})_n \qquad (IV)$$

wherein $R^3$ is as defined below, and $n$ is an integral number from about 2 to about 1000. These polymeric compounds are described in the patent literature, for example, U.S. Pat. No. 3,021,302 col. 1, line 60 to col. 1, line 17; U.S. Pat. No. 3,424,712 col. 3, line 34 to col. 4, line 2; and U.S. Pat. No. 3,424,717, col 3, line 13 to col. 4, line 21. Specific reference is made to these patents at the referenced columns for more details. Other polymeric tin mercaptide type compounds having the —C—Sn—S bonds characterizing the organotin sulfur-containing compounds suitable for use in this invention are exemplified in U.S. Pat. Nos. 2,809,956; 3,293,273; 3,396,185 and 3,485,794 and these exemplifications are incorporated herein by reference.

Preferred organotin stabilizers are described by formula $$R^3Sn(SR^4)_a \qquad (V)$$
$$\underset{Z}{|}$$

wherein:

$a$ is 1 or 2

$R^3$ is a hydrocarbon radical having 1–18 carbon atoms and is selected from the group consisting of alkyl, cycloalkyl, aryl, mixed alkyl-aryl and said hydrocarbon radical having a substituent selected from the group consisting of —CN, —OR$^5$, $$-\overset{O}{\underset{}{\overset{\|}{C}}}R^5,$$

or —CO$_2$R$^5$ where R$^5$ is a 1–20 carbon atom alkyl, alkenyl, cycloalkyl, aryl or mixed alkyl-aryl group;

$R^4$ is a hydrocarbon radical having from 1–22 carbon atoms and is selected from the group consisting of alkyl, cycloalkyl, aryl, mixed alkyl-aryl and said hydrocarbon radical having a substituent selected from the group consisting of —OH, —OR$^5$, $$-O-\overset{O}{\underset{}{\overset{\|}{C}}}R^5$$

and —CO$_2$R$^5$.

Z is O,S,R$^3$, or —SR$^4$

The nature of $R^3$ has in most cases only a minor influence on the performance of the end product. Examples of the group $R^3$ are methyl, ethyl, propyl, butyl, amyl, hexyl, octyl, lauryl, allyl, benzyl, phenyl, tolyl, naphthyl, and cyclohexyl, or a substituted hydrocarbon radical such as 2-carbomethoxyethyl, cyanoethyl (of the type described in U.S. Pat. No. 3,471,538) and the like.

The group SR$^4$ of formula IV may be derived from a mercaptan, or a mercapto alcohol, or an ester of a mercapto alcohol or mercapto acid. Aliphatic and aromatic mercaptans may be employed to form the group SR$^4$. In the case of aliphatic mercaptans, those having 8 to 18 carbon atoms, e.g., decyl or dodecyl mercaptan, are usually preferred because the lower mercaptans are unsuitable for the preparation and use of the stabilizers on account of their offensive smell. Suitable aromatic mercaptans are, for instance, thionaphthol, thiobenzyl alcohol, phenoxyethyl mercaptan, phenoxyethoxyethyl mercaptan and others. As examples of suitable mercapto alcohols, monothioethylene glycol, monothiopropylene glycol, thioglycerol, thiodiethylene glycol, and others may be mentioned. Particularly suitable are the esters of these mercapto alcohols in which the hydroxy groups are esterified by an aliphatic, aromatic, or alicyclic saturated or unsaturated monocarboxylic acid. Readily available mercaptoacid esters are the esters of thioglycolic acid, such as ethyl thioglycolate, isooctylthioglycolate, and generally the esters of mono and dibasic aliphatic and aromatic mercaptoacids, such as esters of beta thiopropionic acid, thiolactic acid, thiobutyric acid and mercapto lauric acid.

Of course, organotin mercaptides, organotin mercapto acids, organotin mercaptoacid esters, etc., per se are not claimed for this invention and the mentioned patents and their specific disclosures clearly teach these compounds and their method of production to enable anyone of ordinary skill to use them in providing the compositions of this invention. Especially preferred examples of organotin stabilizers are as follows:

$(CH_3)_2Sn(SCH_2CO_2C_8H_{17})_2$
$(CH_3)_2Sn(SCH_2CH_2CO_2C_8H_{17})_2$
$CH_3Sn(SCH_2CO_2C_8H_{17})_3$
$CH_3Sn(SCH_2CH_2CO_2C_8H_{17})_3$ $(C_4H_9)_2Sn(SCH_2CO_2C_8H_{17})_2$
$(C_4H_9)_2Sn(SCH_2CH_2CO_2C_8H_{17})_2$
$C_4H_9Sn(SCH_2CO_2C_8H_{17})_3$
$C_4H_9Sn(SCH_2CH_2CO_2C_8H_{17})_3$ $(CH_3)_2Sn(SCHCO_2C_4H_9)_2$
      $|$
      $CH_2CO_2C_4H_9$ $(C_4H_9)_2Sn(SCHCO_2C_4H_9)_2$
      $|$
      $CH_2CO_2C_4H_9$ $CH_3Sn(SCHCO_2C_4H_9)_3$
   $|$
   $CH_2CO_2C_4H_9$ $C_4H_9Sn(SCHCO_2C_4H_9)_3$
   $|$
   $CH_2CO_2C_4H_9$ $(CH_3)_2Sn(SCH_2CO_2C_{13}H_{27})_2$
$CH_3Sn(SCH_2CO_2C_{13}H_{27})_3$
$(C_8H_{17})_2Sn(SCH_2CO_2C_8H_{17})_2$
$(C_8H_{17})_2Sn(SCH_2CH_2CO_2C_8H_{17})_2$
$C_8H_{17}Sn(SCH_2CO_2C_8H_{17})_3$
$C_8H_{17}Sn(SCH_2CH_2CO_2C_8H_{17})_3$ $(C_4H_9)_2Sn(SCH_2CO_2C_{13}H_{27})_2$
$C_4H_9Sn(SCH_2CO_2C_{13}H_{27})_3$
$(CH_3)_2Sn(SC_{12}H_{25})_2$
$(C_4H_9)_2Sn(SC_{12}H_{25})_2$
$(CH_3)_2Sn(SCH_2CH_2O_2CC_{17}H_{35})_2$
$(CH_3)_2Sn(SCH_2CH_2O_2CC_{17}H_{33})_2$ $(C_8H_{17})_2Sn(SCHCO_2C_4H_9)_2$
      $|$
      $CH_2CO_2C_4H_9$ $CH_3Sn(SCH_2CH_2O_2CC_{17}H_{35})_3$ $CH_3Sn(SCH_2CH_2O_2CC_{17}H_{33})_3$ $C_8H_{17}Sn(SCHCO_2C_4H_9)_3$
   $|$
   $CH_2CO_2C_4H_9$ $(C_4H_9)_2Sn(SCH_2CH_2O_2CC_{17}H_{35})_2$ $(C_4H_9)_2Sn(SCH_2CH_2O_2CC_{17}H_{33})_2$ $C_4H_9Sn(SCH_2CH_2O_2CC_{17}H_{35})_3$
$C_4H_9Sn(SCH_2CH_2O_2CC_{17}H_{33})_3$

A mixture of two or more sulfur-containing organotin compounds, e.g., 80 parts of dimethyltin bis (isoctyl thioglycolate) plus 20 parts of methyltin tris (isoctyl thioglycolate) is also operable and part of this invention.

The sulfur-containing antimony compounds which are of use in this invention include those described in U.S. Pat. No. 3,887,508; column 2, line 49 to column 4, line 34 and are generally characterized as having Sb-S group or linkage. Generally, the antimony compounds suitable for use in this invention are derived from trivalent antimony and may be described by the following formula:

$R^3{}_nSb(SR^4)_{3-n}$ 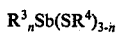

wherein:
$n$ is an integer from 0–2; and,
$R^3$ and $R^4$ are as previously described herein.

Other antimony stablizers suitable for use in this invention are exemplified in U.S. Pat. Nos. 2,680,726; 2,684,956; 3,340,285; 3,399,220; 3,466,261 and 3,530,158.

Especially preferred examples of antimony organic sulfur-containing compounds are:

| | |
|---|---|
| $Sb(SCH_2CO_2C_8H_{17})_3$ | $Sb(SCH_2CH_2O_2CC_{17}H_{35})_3$ |
| $Sb(SCH_2CH_2CO_2C_8H_{17})_3$ | $Sb(SCHCO_2C_4H_9)_3$ $\quad\ \ \ \|$ $\quad\ \ \ CH_2CO_2C_4H_9$ |
| $Sb(SCH_2CH_2O_2CC_{17}H_{33})_3$ | $Sb(SC_{12}H_{25})_3$ |

The stabilizer composition of this invention can be used over a range of about 0.05 to about 10 phr (that is, parts by weight per 100 parts) of halogenated resin. The preferred range is about 0.25 to about 5.0 phr. The two-component system of this invention consists of salt and organotin or antimony stabilizer in the weight ratios of about 0.05:1 to about 3:1 with ratios of 0.1:1 to 2:1 being preferred.

The salts of this invention are especially useful in three-component stabilizer systems containing salt, sulfur-containing organotin or antimony stabilizers, and an overbased organic complex of an alkali or alkaline earth metal base.

The overbased organic complexes are described in U.S. Pat. Nos.; 2,616,904, 2,616,905 2,616,906 2,616,911 2,616,924 2,616,925 2,617,049 2,695,910 2,723,234 2,767,209 2,777,874 2,798,852 2,839,470 2,883,340 2,915,517 2,959,551 2,968,642 2,971,014 2,989,463 3,001,981 3,027,325 3,108,960 3,147,232 3,172,855 3,194,823 3,232,883 3,242,079 3,242,080 3,256,186 3,274,135 3,350,308
and their use in combination with organotins is described in U.S. Pat. Nos. 3,803,083 and U.S. Pat. No. 3,764,571.

The disclosures of these patents relating to overbased organic complexes and the methods for their manufacture are incorporated herein by reference.

Preferred salts, sulfur-containing organotin stabilizers, and antimony stabilizers, are as previously given. Preferred overbased organic complexes are those overbased with $CaCO_3$ and $BaCO_3$; especially preferred is $BaCO_3$.

The three components are generally used in the following amounts.

| Wt.% | |
|---|---|
| 2-50 | salt |
| 30-90 | Sulfur-containing organotin or antimony stabilizer |
| 2-60 | Overbased organic complex of an alkali or alkaline earth metal base |

Preferred ranges are

| Wt.% | |
|---|---|
| 5-40 | salt |
| 40-80 | Sulfur-containing organotin or antimony stabilizer |
| 5-50 | Overbased organic complex of an alkali or alkaline earth metal base |

Particularly useful three-component systems are

| Wt. % | | |
|---|---|---|
| 5-40 | $Ba(SCH_2CO_2C_8H_{17})_2$ or $Ba(SCH_2CH_2O_2CC_{17}H_{35})_2$ | or $Ba(SCH_2CH_2O_2CC_{17}H_{33})_2$ |
| 40-80 | $(CH_3)_2Sn(SCH_2CO_2C_8H_{17})_2$ or | or $(C_4H_9)_2Sn(SCH_2CO_2C_8H_{17})_2$ |
| | $(CH_3)_2Sn(SCH{-}CO_2C_4H_9)_2$ $\quad\quad\,\,\vert$ $\quad\quad CH_2{-}CO_2C_4H_9$ | or $Sb(SCH_2CO_2C_8H_{17})_3$ |
| | or $CH_3Sn(SCH_2CO_2C_8H_{17})_3$ or $CH_3Sn(SCH_2CH_2O_2CC_{17}H_{35})_3$ or $CH_3Sn(SCH_2CH_2O_2CC_{17}H_{33})_3$ | or $Sb(SCH_2CH_2O_2CC_{17}H_{33})_3$ or $Sb(SCH_2CH_2O_2CC_{17}H_{35})_3$ |
| 5-50 | $BaCO_3$ (overbased organic complex) | |

The novel stabilizer compositions of this invention can be used with halogen containing vinyl and vinylidene resins in which the halogen is attached directly to the carbon atoms, as described in U.S. Pat. No. 3,925,309.

As the halogen resin, there can be employed chlorinated polyethylene having 14 to 75%, e.g. 27% chlorine by weight, polyvinyl chloride, polyvinylidene chloride, polyvinyl bromide, polyvinyl fluoride, polyvinylidene fluoride, copolymers of vinyl chloride with 1 to 90%, preferably, 1 to 30% of a copolymerizable ethylenically unsaturated material such as vinyl acetate, vinyl butyrate, vinyl benzoate vinylidene chloride, diethyl fumarate, diethyl maleate, other alkyl fumarates and maleates, vinyl propionate, methyl acrylate, 2-ethylhexyl acrylate, butyl acrylate and other alkyl acrylates, methyl methacrylate, ethyl methacrylate, butyl methacrylate and other alkyl methacrylates, methyl alpha chloroacrylate, styrene, trichloroethylene, vinyl ethers such as vinyl ethyl ether, vinyl chloroethyl ether and vinyl phenyl ether, vinyl ketones such as vinyl methyl ketone and vinyl phenyl ketone, 1-fluoro-1-chloroethylene, acrylonitrile, chloroacrylonitrile, allylidene diacetate and chloroallylidene diacetate. Typical copolymers include vinyl chloride-vinyl acetate (96:4 sold commercially as VYNW), vinyl chloride-vinyl acetate (87:13), vinyl chloride-vinyl acetate-maleic anhydride (86:13:1), vinyl chloride-vinylidene chloride (95:5), vinyl chloride-diethyl fumarate (95:5), vinyl chloride-trichloroethylene (95:5), vinyl chloride-2-ethylhexyl acrylate (80:20).

Preferably, the halogen containing resin is a vinyl halide resin, specifically a vinyl chloride resin.

The stabilizer composition of the present invention can be incorporated with the resin by admixing in an appropriate mill or mixer or by any of the other well-known methods which provide for uniform distribution throughout the resin compositions. Thus, mixing can be accomplished by milling on rolls at 100°–160° C.

In addition to the novel stabilizers, there can also be incorporated with the resin conventional additives such as plasticizers, conventional stabilizers, antioxidants, pigments, fillers, dyes, ultraviolet light absorbing agents, densifying agents and the like as identified and in the amounts set forth in U.S. Pat. No. 3,925,309.

The invention will be further understood by reference to the following examples which serve to illustrate, but not limit, the invention.

Examples 1–5 illustrate the preparation of the alkali and alkaline earth metal mercaptides.

EXAMPLE 1

Preparation of Barium bis (dodecyl mercaptide)

In a three-necked, round-bottomed flask, equipped with a condenser, addition funnel and a stopper, a barium methoxide solution is prepared by dissolving 12.1g (0.088g-atom) of barium metal in 200 ml of methanol under a nitrogen atmosphere. To the stirred barium methoxide solution is added a solution of 35.7 g (0.176 mole) of dodecyl mercaptan in 100 ml of methanol. The mixture is stirred at room temperature for 0.5 hour. The solvent is vacuum stripped to give 44.2 g of product (93.0% yield). Infrared data is consistent with the assigned structure.

Anal. Calcd. for $C_{24}H_{50}S_2Ba$: C, 53.3; H, 9.33; S, 11.9; Ba, 25.4

Found: C, 51.7; H, 9.34; S, 10.1; Ba, 23.8

EXAMPLE 2

Preparation of Barium bis (isooctyl thioglycolate)

The apparatus and procedure used are the same as described in Example 1. A solution of 40.1 g (0.196 mole) of isooctyl thioglycolate dissolved in 100 ml of methanol is added to a solution of 19.6 g (0.0981 mole) of barium methoxide in 200 ml of methanol. The mixture is stirred at 0° C for 2 hours. The solvent is vacuum stripped to give 52.1 g of product (97.6% yield). The infrared data is consistent with the assigned structure.

Anal. Calcd. for $C_{20}H_{38}O_4S_2Ba$: S(mercapto), 11.8

Found: S(mercapto), 11.1

EXAMPLE 3

Preparation of Barium S,O-3-mercaptopropionate

The apparatus and procedure used are the same as described in Example 1. A solution of 11.6g (0.109 mole) of 3-mercaptopropionic acid dissolved in 100 ml of methanol is added to a solution of 21.7 g (0.109 mole) of barium methoxide in 200 ml of methanol. The mixture is stirred at room temperature for three hours and then filtered to collect the solid product. The yield of product is essentially quantitative. The infrared data is consistent with the assigned structure.

Anal. Calcd. for $C_3H_4O_2SBa$: C, 14.9; H, 1.67; S, 13.3; Ba, 56.9

Found: C, 14.7; H, 2.41; S, 11.7; Ba, 52.6

EXAMPLE 4

Preparation of Calcium bis (isooctyl thioglycolate)

In a three-necked, round-bottomed flask, equipped with a condenser, mechanical stirrer and stopper, a calcium ethoxide solution is prepared by heating a mixture of 12.1 g (0.3 g-atom) of calcium turnings and 400 ml of ethanol under a nitrogen atomsphere. When the calcium dissolves, the ethanol is removed by distillation and 38.6 g (98.2%) of calcium ethoxide is isolated. To a stirred suspension of 13.1 g (0.1 mole) of calcium ethoxide in 65 ml of petroleum ether is added a solution of 40.9 g (0.2 mole) of isooctyl thioglycolate in 65 ml of petroleum ether. The mixture is stirred at 0° C for 1 hour. The solvent is vacuum stripped to give an essentially quantitative yield of product. The infrared data is consistent with the assigned structure.

Anal. Calcd. for $C_{20}H_{38}O_4S_2Ca$: C, 53.7; H, 8.57; Ca, 8.95

Found: C, 52.3; H, 8.73; Ca, 7.65

EXAMPLE 5

Preparation of Sodium isooctyl thioglycolate

In a three-necked, round-bottomed flask, equipped with a condenser, addition funnel, and a stopper, a solution of sodium methoxide is prepared by dissolving 7.0 g (0.305 g-atom) of sodium in 250 ml of methanol under a nitrogen atmosphere. To the stirred sodium methoxide solution is added a solution of 62.3 g (0.305 mole) of isooctyl thioglycolate in 100 ml of methanol. The resulting mixture is stirred at 0° C for 2 hours. The solvent is vacuum stripped to give the product in essentially quantitative yield. The infrared data is consistent with the assigned structure.

Anal. Calcd. for $C_{10}H_{19}O_2SNa$: S(mercapto), 14.2
Found: S(mercapto), 11.2

EXAMPLES 6-37

In the following Examples, a standard single-screw pipe formulation is used which contains 100 parts by weight of a polyvinyl chloride homopolymer (VC 100 PM, Borden Chemical Co.); 3.0 parts by weight of a processing aid which is an acrylic polymer consisting of 90% methyl methacrylate and 10% ethyl acrylate (K-120N, Rohm and Haas Co.); 0.5 parts by weight of a paraffin wax (Rosswax 165, F. B. Ross Co.); 0.2 parts by weight of a partially saponified ester wax (Wax OP, American Hoechst Co.); 1.4 parts by weight of calcium stearate: 2.0 parts by weight of titanium dioxide; and stabilizer as indicated (all amounts in parts by weight). The resin mixtures are dryblended in a Waring Commercial Blender and their dynamic heat stability determined on a Brabender Plastograph using a 67.5 g charge, 415° F(213° C) stock temperature, and 40 rpm mixing head speed. The dynamic heat stability (failure time) of the polymer mixture is reported as the number of minutes from the point of polymer fusion to the onset of degradation. Organotin stabilizers are abbreviated as follows:

DBTG — Dibutyltin bis (isooctyl thioglycolate)
DMMS — Dimethyltin bis (dibutyl mercaptosuccinate)
DMTG — Dimethyltin bis (isooctyl thioglycolate)
MTG — Methyltin tris (isooctyl thioglycolate)
MTMS — methyltin tris (2-mercaptoethyl stearate)
ATG — Antimony tris (isooctyl thioglycolate)

TABLE I

| Example No. | Parts | Stabilizer | Failure (Min) |
|---|---|---|---|
| 6 | 1.5 | DBTG | 20 |
| 7 | 1.5 | barium bis (isooctyl thioglycolate) | 4 |
| 8 | 1.5 | DBTG | 37 |
|   | 1.5 | barium bis (isooctyl thioglycolate) |   |
| 9 | 1.1 | DBTG | 22 |
|   | 0.4 | barium bis (isooctyl thioglycolate) |   |
| 10 | 0.75 | DBTG | 14 |
| 11 | 0.75 | barium bis (isooctyl thioglycolate) | 2 |
| 12 | 0.75 | DBTG | 21 |
|   | 0.75 | barium bis (isooctyl thioglycolate) |   |
| 13 | 0.75 | barium bis (dodecyl mercaptide) | 1 |
| 14 | 1.1 | DBTG | 21 |
|   | 0.4 | barium bis (dodecyl mercaptide) |   |
| 15 | 0.75 | DBTG | 20 |
|   | 0.75 | barium bis (dodecyl mercaptide) |   |
| 16 | 1.5 | DMMS | 24 |
| 17 | 0.75 | DMMS | 13 |
| 18 | 0.75 | DMMS | 24 |
|   | 0.75 | barium bis (isooctyl thioglycolate) |   |
| 19 | 0.75 | DMMS | 24 |
|   | 0.75 | barium bis (isooctyl3-mercaptopropionate) |   |
| 20 | 0.75 | DMMS | 22 |
|   | 0.75 | calcium bis (isooctyl thioglycolate) |   |
| 21 | 0.75 | DMMS | 22 |
|   | 0.75 | calcium bis (isooctyl 3-mercaptopropionate) |   |
| 22 | 0.75 | DMMS | 26 |
|   | 0.75 | barium S,O-thioglycolate |   |
| 23 | 0.75 | barium S,O-3-mercaptopropionate | 4 |
| 24 | 0.75 | DMMS | 28 |
|   | 0.75 | barium S,O-3-mercaptopropionate |   |
| 25 | 0.75 | DMMS | 24 |
|   | 0.75 | calcium S,O-thioglycolate |   |
| 26 | 0.75 | DMMS | 25 |
|   | 0.75 | calcium S,O-3-mercaptopropionate |   |

TABLE I-continued

| Example No. | Parts | Stabilizer | Failure (Min) |
|---|---|---|---|
| 27 | 0.75 | DMMS | 17 |
|  | 0.75 | sodium isooctyl 3-mercaptopropionate |  |
| 28 | 0.75 | DMMS | 22 |
|  | 0.75 | disodium S,O-thioglycolate |  |
| 29 | 0.75 | DMMS | 19 |
|  | 0.75 | disodium S,O-3-mercaptopropionate |  |
| 30 | 1.5 | DMTG | 21 |
| 31 | 0.75 | DMTG | 22 |
|  | 0.75 | barium bis (isooctyl thioglycolate) |  |
| 32 | 1.5 | MTG | 13 |
| 33 | 0.75 | MTG | 16 |
|  | 0.75 | barium bis (isooctyl thioglycolate) |  |
| 34 | 1.5 | MTMS | 19 |
| 35 | 1.0 | MTMS | 18 |
|  | 0.5 | barium bis (2-mercaptoethyl stearate) | 18 |
| 36 | 0.75 | ATG | 12 |
| 37 | 0.75 | ATG | 18 |
|  | 0.75 | barium bis (isooctyl thioglycolate) |  |

These results demonstrate the dramatic and unexpected synergistic effect resulting from the combination of expensive organotin and antimony stabilizers with less-expensive alkali and alkaline-earth metal mercaptides.

EXAMPLE 38

Preparation of Barium Carbonate Dispersion (Overbased Organic Complex)

In a three-necked, round-bottomed flask equipped with a mechanical stirrer, Dean-Stark trap, and a stopper, a stirred mixture of: 57g of nitrated polyisobutylene; 133g of a light paraffin oil; 50g of isooctyl alcohol; 60.8g (0.28 eq.) of p-nonylphenol; and 138.7g (1.6.eq.) of barium hydroxide monohydrate is heated to 150° C and maintained at that temperature for five hours to drive off the water. Thereupon, the reaction mixture is gassed with carbon dioxide at a rate of 19g/hr. for 3 hours at 150° C. The isooctyl alcohol and excess water is then vacuum stripped and the product filtered. The yield of product, a dark viscous solution, is 341.3g (84.5%).

Theory: Ba, 27.7%; $CO_3^{-2}$, 10.0%
Found: Ba, 23.1%; $CO_3^{-2}$, 8.45%.

Examples of three component systems are given in Table 2. Performance tests are as described for Examples 6–37.

This data further demonstrates the unexpected improvement and synergistic effect resulting from the combination of the composition of this invention with an over-based organic complex of an alkali or alkaline earth metal carbonate. Methyltin tris (2-mercaptoethyl oleate) is abbreviated MTMO.

TABLE 2

| Example No. | Parts | Stabilizer | Failure (Min) |
|---|---|---|---|
| 39 | 1.5 | DBTG | 11 |
| 40 | 0.52 | $BaCO_3$ dispersion | 4 |
| 41 | 1.2 | DBTG | 31 |
|  | 0.3 | $BaCO_3$ dispersion |  |
| 42 | 0.75 | DBTG | 34 |
|  | 0.52 | $BaCO_3$ dispersion |  |
|  | 0.23 | barium bis (isooctyl thioglycolate) |  |
| 43 | 0.5 | DBTG | 21 |
|  | 0.17 | $BaCO_3$ dispersion |  |
|  | 0.08 | barium bis (isooctyl thioglycolate) |  |
| 44 | 1.5 | DMTG | 21 |
| 45 | 0.75 | DMTG | 40 |
|  | 0.52 | $BaCO_3$ dispersion |  |
|  | 0.23 | barium bis (isooctyl thioglycolate) |  |
| 46 | 1.5 | DMMS | 24 |
| 47 | 0.75 | DMMS | 40 |
|  | 0.52 | $BaCO_3$ dispersion |  |
|  | 0.23 | barium bis (isooctyl thioglycolate) |  |
| 48 | 0.75 | DMMS | 35 |
|  | 0.38 | $BaCO_3$ dispersion |  |
|  | 0.37 | sodium isooctyl thioglycolate |  |
| 49 | 0.75 | DMMS | 27 |
|  | 0.37 | $BaCO_3$ dispersion |  |
|  | 0.38 | calcium bis (isooctyl 3-mercaptopropionate) |  |
| 50 | 1.5 | MTMO | 17 |
| 51 | 0.8 | MTMO | 22 |
|  | 0.35 | $BaCO_3$ dispersion |  |
|  | 0.35 | barium bis (2-mercaptoethyl oleate) |  |
| 52 | 1.5 | ATG | 15 |
| 53 | 0.75 | ATG | 16 |
|  | 0.375 | $BaCO_3$ dispersion |  |
|  | 0.375 | barium bis (isooctyl thioglycolate) |  |

We claim:
1. A composition of matter comprising a mixture of (a) an alkali or alkaline earth metal salt of a mercaptan or mercapto acid and (b) a sulfur-containing organotin compound having a

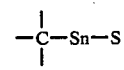

group, or a sulfur-containing antimony compound having a Sb—S group, said mixture having a weight ratio of (a) to (b) ranging between about 0.05:1 and about 3:1.

2. The composition of claim 1 wherein said alkali or alkaline earth metal salt of mercaptan or mercapto acid has a formula selected from the group consisting of

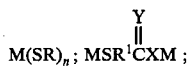

and

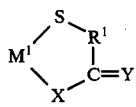

where
M is an alkali or alkaline earth metal;
$M^1$ is an alkaline earth metal;
n is 1 when M is an alkali metal;
n is 2 when M is alkaline earth metal;
R is a hydrocarbon radical having from 1 to 22 carbon atoms and is selected from the group consisting of alkyl, cycloalkyl, aryl, mixed alkyl-aryl and said hydrocarbon radicals having a substituent selected from the group consisting of halogen, —XH, —$XR^2$,

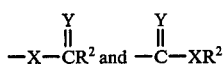

where $R^2$ is a hydrocarbon radical having from 1-20 carbon atoms and is selected from the group consisting of alkyl, alkenyl, cycloalkyl, aryl and mixed alkyl-aryl;
$R^1$ is a divalent hydrocarbon radical having from 1 to 6 carbon atoms or said divalent hydrocarbon radical having a substituent as described for R; and
X and Y are independently selected from the group consisting of oxygen and sulfur.

3. The composition of claim 1 wherein said sulfur-containing organotin compound has the formula:

and said sulfur-containing antimony compound has the formula:

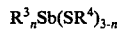

where
$R^3$ is a hydrocarbon radical having from 1 to 18 carbon atoms and is selected from the group consisting of alkyl, cycloalkyl, aryl, mixed alkyl-aryl and said hydrocarbon radical having a substituent selected from the group consisting of —CN, —$OR^5$,

or —$CO_2R^5$ where $R^5$ is a 1-20 carbon atom alkyl, aryl, cycloalkyl, alkenyl, or mixed alkyl-aryl group:
$R^4$ is a hydrocarbon radical having from 1 to 22 carbon atoms and is selected from the group consisting of alkyl, cycloalkyl, aryl, mixed alkyl-aryl and said hydrocarbon radicals having a substituent selected from the group consisting of —OH, —$OR^5$,

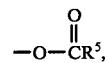

and —$CO_2R^5$;
Z is selected from the group consisting of oxygen, sulfur, —$R^3$ and —$SR^4$;
a is 1 when Z is oxygen or sulfur and 2 when Z is —$R^3$ or —$SR^4$; and
n is an integer from 0-2.

4. The composition of claim 2 wherein
M is selected from the group consisting of sodium, calcium and barium;
$M^1$ is selected from the group consisting of calcium and barium,
$R^3$ has from 1 to 8 carbon atoms;
Z is $R^3$ or —$SR^4$, and
$R^4$ is selected from the group consisting of —$CH_2COOR^5$, —$CH_2CH_2COOR^5$,

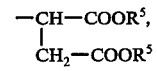

—$(CH_2)_2O_2CR^5$
and —$(CH_2)_3O_2CR^5$.

5. The composition of claim 4 wherein $M(SR)_n$ is selected from the group consisting of:

$Ba(SCH_2CO_2C_8H_{17})_2$, $Ba(SCH_2CH_2O_2CC_{17}H_{33})_2$,
$Ba(SCH_2CH_2O_2CC_{17}H_{35})_2$, $Ca(SCH_2CO_2C_8H_{17})_2$,
$Ca(SCH_2CH_2O_2CC_{17}H_{33})_2$, $Ca(SCH_2CH_2O_2CC_{17}H_{35})_2$ and
$NaSCH_2CO_2C_8H_{17}$, and

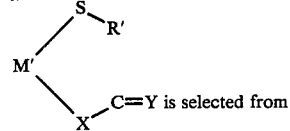

is selected from the group consisting of

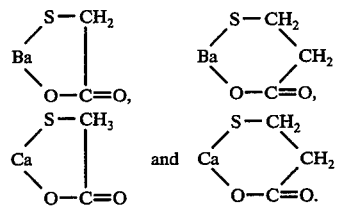

6. The composition of claim 3 wherein

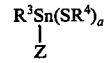

is selected from the group consisting of:
$CH_3Sn(SCH_2CO_2C_8H_{17})_3$,
$CH_3Sn(SCH_2CH_2O_2CC_{17}H_{33})_3$,
$CH_3Sn(SCH_2CH_2O_2CC_{17}H_{35})_3$,
$(CH_3)_2Sn(SCH_2CO_2C_8H_{17})_2$,
$(CH_3)_2Sn(SCH_2CH_2O_2CC_{17}H_{33})_2$,
$(CH_3)_2Sn(SCH_2CH_2O_2CC_{17}H_{35})_2$,

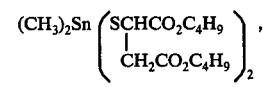

$(C_4H_9)_2Sn(SCH_2CO_2C_8H_{17})_2$ and
$(C_8H_{17})_2Sn(SCH_2CO_2C_8H_{17})_2$; and
$R^3{}_nSb(SR^4)_{3-n}$
is selected from the group consisting of:
$Sb(SCH_2CO_2C_8H_{17})_3$,
$Sb(SCH_2CH_2CO_2C_8H_{17})_3$,
$Sb(SCH_2CH_2O_2CC_{17}H_{33})_3$
$Sb(SCH_2CH_2O_2CC_{17}H_{35})_3$ and $$Sb(SCHCO_2C_4H_9)_3.$$
$$\quad\quad |$$
$$\quad CH_2Cl_2C_4H_9$$

7. The composition of claim 1 additionally containing an over-based organic complex of an alkaline earth metal carbonate in an amount sufficient to provide additional heat stability to a halogenated resin to which said composition is added.

8. The composition of claim 6 additionally containing an over-based organic complex of an alkaline earth metal base selected from the group consisting of $BaCO_3$ and $CaCO_3$, and said composition having the following range of proportions totaling 100 percent by weight:

| Percent | Component |
|---|---|
| a) 2-50 | salt of mercaptan or mercapto acid, |
| b) 30-90 | organotin or antimony compound, and |
| c) 2-60 | over-based organic complex |

9. The composition of claim 8 wherein the components are selected from the group consisting of the following listed components and used in the given proportions:

| | Percent | Component | |
|---|---|---|---|
| a) | 5-40 | $Ba(SCH_2CO_2C_8H_{17})_2$, $Ba(SCH_2CH_2O_2CC_{17}H_{33})_2$ or $Ba(SCH_2CH_2O_2CC_{17}H_{35})_2$ | |
| | | Sn | Sb |
| b) | 40-80 | $CH_3Sn(SCH_2CO_2C_8H_{17})_3$, $CH_3Sn(SCH_2CH_2O_2CC_{17}H_{33})_3$, $CH_3Sn(SCH_2CH_2O_2CC_{17}H_{35})_3$, $(CH_3)_2Sn(SCH_2CO_2C_8H_{17})_2$, $(CH_3)_2Sn(SCHCO_2C_4H_9)_2$, \| CH_2CO_2C_4H_9 $(C_4H_9)_2Sn(SCH_2CO_2C_8H_{17})_2$, | $Sb(SCH_2CO_2C_8H_{17})_3$, $Sb(SCH_2CH_2CO_2C_8H_{17})_3$, $Sb(SCH_2CH_2O_2CC_{17}H_{33})_3$, $Sb(SCH_2CH_2O_2CC_{17}H_{35})_3$ $Sb\begin{pmatrix} SCHCO_2C_4H_9 \\ \| \\ CH_2CO_2C_4H_9 \end{pmatrix}_3$ |
| c) | 5-50 | over-based organic complex of $BaCO_3$ | |

10. The composition of claim 1 dispersed in a halogen containing vinyl or vinylidene resin in which the halogen is attached directly to at least one carbon atom, said composition dispersed in said resin in an amount sufficient to improve the heat stability thereof.

11. The composition of claim 1 dispersed in a resin of vinyl chloride homopolymer or copolymer of vinyl chloride with from about 1 to about 30 percent of at least one copolymerizable ethylenically unsaturated monomer, said composition dispersed in said resin in an amount sufficient to improve the heat stability thereof.

12. The composition of claim 6 dispersed in a halogen containing vinyl or vinylidene resin in which the halogen is attached directly to at least one carbon atom, said composition dispersed in said resin in an amount sufficient to improve the heat stability thereof.

13. The composition of claim 6 dispersed in a resin of vinyl chloride homopolymer or copolymer of vinyl chloride with from about 1 to about 30 percent of at least one copolymerizable ethylenically unsaturated monomer, said composition dispersed in said resin in an amount sufficient to improve the heat stability thereof.

14. The composition of claim 8 dispersed in a halogen containing vinyl or vinylidene resin in which the halogen is attached directly to at least one carbon atom, said composition dispersed in said resin in an amount sufficient to improve the heat stability thereof.

15. The composition of claim 8 dispersed in a resin of vinyl chloride homopolymer or copolymer of vinyl chloride with from about 1 to about 30 percent of at least one copolymerizable ethylenically unsaturated monomer, said composition dispersed in said resin in an amount sufficient to improve the heat stability thereof.

16. The composition of claim 9 dispersed in a halogen containing vinyl or vinylidene resin in which the halogen is attached directly to at least one carbon atom, said composition dispersed in said resin in an amount sufficient to improve the heat stability thereof.

17. The composition of claim 9 dispersed in a resin of vinyl chloride homopolymer or copolymer of vinyl chloride with from about 1 to about 30 percent of at least one copolymerizable ethylenically unsaturated monomer, said composition dispersed in said resin in an amount sufficient to improve the heat stability thereof.

18. The composition of claim 9 dispersed in a resin of vinyl chloride homopolymer or copolymer of vinyl chloride with from about 1 to about 30 percent of at least one copolymerizable ethylenically unsaturated monomer, said composition dispersed in said resin in an amount ranging from about 0.05 to about 10 parts of said composition in each 100 parts of said resin.

* * * * *

UNITED STATES PATENT OFFICE
CERTIFICATE OF CORRECTION

Patent No. 4,115,352     Dated September 19, 1978

Inventor(s) Joseph Michael Bohen, Sameeh Said Toukan

It is certified that error appears in the above-identified patent and that said Letters Patent are hereby corrected as shown below:

In Claim 5, line 45,

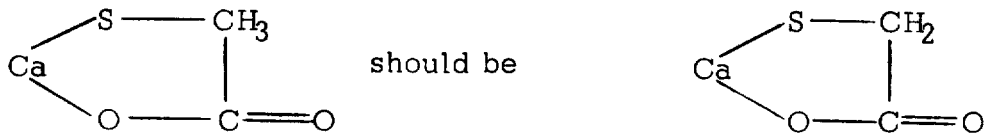

Column 19, lines 10 - 11, the formula,

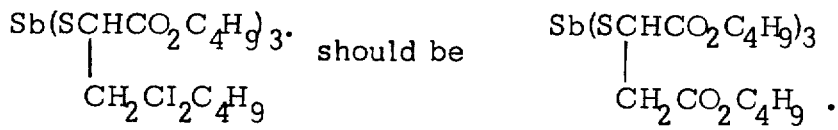

Signed and Sealed this

Third Day of July 1979

[SEAL]

Attest:

Attesting Officer

LUTRELLE F. PARKER
Acting Commissioner of Patents and Trademarks